# (12) United States Patent
Kino et al.

(10) Patent No.: US 7,547,440 B2
(45) Date of Patent: Jun. 16, 2009

(54) T-CELL EPITOPE PEPTIDES

(75) Inventors: Kohsuke Kino, Kanagawa (JP); Kazuo Dairiki, Kanagawa (JP)

(73) Assignee: Meiji Dairies Corporation (JP)

( * ) Notice: Subject to any disclaimer, the term of this patent is extended or adjusted under 35 U.S.C. 154(b) by 0 days.

(21) Appl. No.: 12/163,896

(22) Filed: Jun. 27, 2008

(65) Prior Publication Data

US 2008/0274972 A1 Nov. 6, 2008

Related U.S. Application Data

(62) Division of application No. 11/354,543, filed on Feb. 14, 2006, now Pat. No. 7,407,657, which is a division of application No. 09/202,464, filed as application No. PCT/JP97/02031 on Jun. 12, 1997, now Pat. No. 7,112,329.

(30) Foreign Application Priority Data

Jun. 14, 1996 (JP) .................................. 8/153527

(51) Int. Cl.
A61K 39/00 (2006.01)
A61K 39/35 (2006.01)
A61K 39/36 (2006.01)
A61K 38/04 (2006.01)

(52) U.S. Cl. ................. 424/185.1; 424/275.1; 530/326; 530/327; 530/328

(58) Field of Classification Search ........................ None
See application file for complete search history.

(56) References Cited

U.S. PATENT DOCUMENTS

| 6,719,976 B1 | 4/2004 | Sone et al. | |
| 7,112,329 B1 * | 9/2006 | Kino et al. | 424/185.1 |
| 7,407,657 B2 * | 8/2008 | Kino et al. | 424/185.1 |

FOREIGN PATENT DOCUMENTS

| EP | 0 655 500 | 5/1995 |
| EP | 0 714 662 | 6/1996 |
| EP | 0 923 940 | 6/1999 |
| JP | 03-275699 | 12/1991 |
| JP | 03-284697 | 12/1991 |
| JP | 06-500308 | 1/1994 |
| JP | 06-508994 | 10/1994 |
| JP | 05-507700 | 11/1994 |
| JP | 07-503362 | 4/1995 |
| JP | 07-118295 | 5/1995 |
| JP | A HEI 8-47392 | 2/1996 |
| JP | 8-502163 | 3/1996 |
| JP | 08-127591 | 5/1996 |
| JP | 08-505284 | 6/1996 |
| JP | 8 176192 | 7/1996 |
| JP | 08-333391 | 12/1996 |
| JP | P3474898 | 12/2003 |
| JP | 05-15427 | 5/2005 |
| JP | 3734040 B2 | 1/2006 |
| WO | WO93/01213 | 1/1993 |
| WO | WO 93/08280 | 4/1993 |
| WO | WO 93/19178 | 9/1993 |
| WO | WO 94/01560 | 1/1994 |
| WO | WO94/11512 | 5/1994 |
| WO | WO 94/11512 | 5/1994 |
| WO | WO 95/27786 | 10/1995 |
| WO | WO97/32600 | 12/1997 |

OTHER PUBLICATIONS

Berzofsky et al., in Fundamental Immunology $2^{nd}$ edition, Raven Press, 1989.
Burks et al., Eur. J. Biochem., 245 :334-339 (1997).
Fasier et al., J Allergy Clin Immunology 101(4): 521-530, Apr. 1998.
Hoyne et al., Immunol and Cell Biology 74 : 180-186 (1996).
Ide et al., Allergy no Rinshou 11(3):174-178 (1991).
Ikagawa et al., "Allergens, IgE, mediators, inflammatory mechanisms . . . " J. Allergy Clin. Immunol., 97 :53-64 (1996).
Ikagawa et al., Single amino acid substitutions on a Japanese cedar pollen allergen (Cry j 1) derived peptide induced alterations in human T cell responses and T cell receptor antagonism, J Allergy Clin Immunol, 97(1 pt 1):53-64, Jan. 1996.
Matsushita et al., "Allele Specificity of Structural Requirement for Peptides . . . Syndrome," J. Exp. Med., 189:873-883 (1994).
Ngo et al., 1994, The Protein Folding Problem and Tertiary Structure Prediction, pp. 492-495.
Okano et al., Allergy 43(9):1179-1184 (1994).
Saito et al., Chiryo 78(2):1571-1576 (1996).
Stanley et al., Archives of Biochemistry and Biophysics, 342(2): 244-253, Jun. 1997.
Stryer et al., in Biochemistry, Third edition, W H Freeman Company, New York, pp. 31-33 (1998).
Suzuki et al., Mol. Immunol., 33(4-5):451-60 (1996).
Swoboda et al., "Isoforms of Bet v 1, the Major Birch Pollen Allergen, Analyzed by Liquid Chromatography, Mass Spectrometry, and cDNA Cloning," J. Biol. Chem., 270(6):2607-2613 (1995).
Taniai et al., "epitopes on Cry j I and Cry j II for the Human IgE antibodies Cross-Reactive . . . Pollen," Mol. Immunol. 30(2):183-189 (1993).
Tokyo Jikeikai Ika Daigaku Zasshi, 111(6):949-956 (1996).
Webster's II New Riverside University Dictionary, p. 933, 1984.
Devlin et al., "Random Peptide Libraries: A Source of Specific Protein Binding Molecules", Science, 249:404-406 (Jul. 1990).

* cited by examiner

*Primary Examiner*—Phuong Huynh
(74) *Attorney, Agent, or Firm*—Fish & Richardson P.C.

(57) ABSTRACT

The T-cell epitope site on a Japanese cypress (hinoki) pollen allergen molecule has been identified by stimulating a T-cell line established from a patient suffering from Japanese cypress pollen allergy with an overlap peptide covering the primary structure of the Japanese cypress pollen allergen. The peptide is useful in peptide-based immunotherapy for patients with spring tree pollinosis including patients with Japanese cypress pollinosis having cross reactivity with Japanese cypress pollen. The peptide is also useful for diagnosing spring tree pollinosis.

6 Claims, 8 Drawing Sheets

| | | |
|---|---|---|
| #1-1(1-20). | D N P I D S C W R G D A N W D Q N R M K | SEQ ID NO: 3 |
| #1-2(11-30). | D A N W D Q N R M K L A D C A V G F G S | SEQ ID NO: 4 |
| #1-3(21-40). | L A D C A V G F G S S A M G G K G G A F | SEQ ID NO: 5 |
| #1-4(31-50). | S A M G G K G G A F Y T V T S S D D D P | SEQ ID NO: 6 |
| #1-5(41-60). | Y T V T S S D D D P V N P A P G T L R Y | SEQ ID NO: 7 |
| #1-6(51-70). | V N P A P G T L R Y G A T R E R S L W I | SEQ ID NO: 8 |
| #1-7(61-80). | G A T R E R S L W I I F S K N L N I K L | SEQ ID NO: 9 |
| #1-8(71-90). | I F S K N L N I K L N M P L Y I A G N K | SEQ ID NO: 10 |
| #1-9(81-100). | N M P L Y I A G N K T I D G R G A E V H | SEQ ID NO: 11 |
| #1-10(91-110). | T I D G R G A E V H I G N G G P C L F M | SEQ ID NO: 12 |
| #1-11(101-120). | I G N G G P C L F M R T V S H V I L H G | SEQ ID NO: 13 |
| #1-12(111-130). | R T V S H V I L H G L N I H G C N T S V | SEQ ID NO: 14 |
| #1-13(121-140). | L N I H G C N T S V S G N V L I S E A S | SEQ ID NO: 15 |
| #1-14(131-150). | S G N V L I S E A S G V V P V H A Q D G | SEQ ID NO: 16 |
| #1-15(141-160). | G V V P V H A Q D G D A I T M R N V T D | SEQ ID NO: 17 |
| #1-16(151-170). | D A I T M R N V T D Y W I D H N S L S D | SEQ ID NO: 18 |
| #1-17(161-180). | V W I D H N S L S D S S D G L V D V T L | SEQ ID NO: 19 |
| #1-18(171-190). | S S D G L V D V T L A S T G V T I S N N | SEQ ID NO: 20 |
| #1-19(181-200). | A S T G V T I S N N H F F N H H K V M L | SEQ ID NO: 21 |
| #1-20(191-210). | H F F N H H K V M L L G H S D I Y S D D | SEQ ID NO: 22 |
| #1-21(201-220). | L G H S D I Y S D D K S M K V T V A F N | SEQ ID NO: 23 |
| #1-22(211-230). | K S M K V T V A F N Q F G P N A G Q R M | SEQ ID NO: 24 |
| #1-23(221-240). | Q F G P N A G Q R M P R A R Y G L I H V | SEQ ID NO: 25 |
| #1-24(231-250). | P R A R Y G L I H V A N N Y D P W S I | SEQ ID NO: 26 |
| #1-25(241-260). | A N N N Y D P W S I Y A I G G S S N P T | SEQ ID NO: 27 |
| #1-26(251-270). | Y A I G G S S N P T I L S E G N S F T A | SEQ ID NO: 28 |
| #1-27(261-280). | I L S E G N S F T A P N D S D K K E V T | SEQ ID NO: 29 |
| #1-28(271-290). | P N D S D K K E V T R R V G C E S P S T | SEQ ID NO: 30 |

FIG. 2

1-29(281-300). R R V G C E S P S T C A N W V W R S T Q  SEQ ID NO: 31
1-30(291-310). C A N W V W R S T Q D S F N N G A Y F V  SEQ ID NO: 32
1-31(301-320). D S F N N G A Y F V S S G K N E G T N I  SEQ ID NO: 33
1-32(311-330). S S G K N E G T N I Y N N N E A F K V E  SEQ ID NO: 34
1-33(321-340). Y N N N E A F K V E N G S A A P Q L T K  SEQ ID NO: 35
1-34(331-350). N G S A A P Q L T K N A G V L T C I L S  SEQ ID NO: 36
1-35(341-354). N A G V L T C I L S K P C S  SEQ ID NO: 37

FIG. 3

| | | |
|---|---|---|
| #1-2(11-30). | D A N W D Q N R M K L A D C A V G F G S | SEQ ID NO: 4 |
| #1-4(31-50). | S A M G G K G G A F Y T V T S S D D D P | SEQ ID NO: 6 |
| #1-5(41-60). | Y T V T S S D D D P V N P A P G T L R Y | SEQ ID NO: 7 |
| #1-6(51-70). | V N P A P G T L R Y G A T R E R S L W I | SEQ ID NO: 8 |
| #1-7(61-80). | G A T R E R S L W I I F S K N L N I K L | SEQ ID NO: 9 |
| #1-8(71-90). | I F S K N L N I K L N M P L Y I A G N K | SEQ ID NO: 10 |
| #1-10(91-110). | T I D G R G A E V H I G N G G P C L F M | SEQ ID NO: 12 |
| #1-11(101-120). | I G N G G P C L F M R T V S H V I L H G | SEQ ID NO: 13 |
| #1-12(111-130). | R T V S H V I L H G L N I H G C N T S V | SEQ ID NO: 14 |
| #1-14(131-150). | S G N V L I S E A S G V V P V H A Q D G | SEQ ID NO: 16 |
| #1-15(141-160). | G V V P V H A Q D G D A I T M R N V T D | SEQ ID NO: 17 |
| #1-16(151-170). | D A I T M R N V T D V W I D H N S L S D | SEQ ID NO: 18 |
| #1-19(181-200). | A S T G V T I S N N H F F N H H K V M L | SEQ ID NO: 21 |
| #1-20(191-210). | H F F N H H K V M L L G H S D I Y S D D | SEQ ID NO: 22 |
| #1-21(201-220). | L G H S D I Y S D D K S M K V T V A F N | SEQ ID NO: 23 |
| #1-22(211-230). | K S M K V T V A F N Q F G P N A G Q R M | SEQ ID NO: 24 |
| #1-23(221-240). | Q F G P N A G Q R M P R A R Y G L I H V | SEQ ID NO: 25 |
| #1-24(231-250). | P R A R Y G L I H V A N N Y D P W S I | SEQ ID NO: 26 |
| #1-25(241-260). | A N N Y D P W S I Y A I G G S S N P T | SEQ ID NO: 27 |
| #1-26(251-270). | Y A I G G S S N P T I L S E G N S F T A | SEQ ID NO: 28 |
| #1-27(261-280). | I L S E G N S F T A P N D S D K K E V T | SEQ ID NO: 29 |
| #1-30(291-310). | C A N W V W R S T Q D S F N N G A Y F V | SEQ ID NO: 32 |
| #1-31(301-320). | D S F N N G A Y F V S S G K N E G T N I | SEQ ID NO: 33 |
| #1-32(311-330). | S S G K N E G T N I Y N N E A F K V E | SEQ ID NO: 34 |
| #1-33(321-340). | Y N N E A F K V E N G S A A P Q L T K | SEQ ID NO: 35 |
| #1-34(331-350). | N G S A A P Q L T K N A G V L T C I L S | SEQ ID NO: 36 |

FIG. 4

| | | |
|---|---|---|
| #2-1( 1-20). | M G M K F M A A V A F L A L Q L I V M A | SEQ ID NO: 38 |
| #2-2(11-30). | F L A L Q L I V M A A A E D Q S A Q I M | SEQ ID NO: 39 |
| #2-3(21-40). | A A E D Q S A Q I M L D S D I E Q Y L R | SEQ ID NO: 40 |
| #2-4(31-50). | L D S D I E Q Y L R S N R S L K K L V H | SEQ ID NO: 41 |
| #2-5(41-60). | S N R S L K K L V H S R H D A A T V F N | SEQ ID NO: 42 |
| #2-6(51-70). | S R H D A A T V F N V E Q Y G A V G D G | SEQ ID NO: 43 |
| #2-7(61-80). | V E Q Y G A V G D G K H D S T E A F A T | SEQ ID NO: 44 |
| #2-8(71-90). | K H D S T E A F A T T W N A A C K K A S | SEQ ID NO: 45 |
| #2-9(81-100). | T W N A A C K K A S A V L L V P A N K K | SEQ ID NO: 46 |
| #2-10(91-110). | A V L L V P A N K K F F V N N L V F R G | SEQ ID NO: 47 |
| #2-11(101-120). | F F V N N L V F R G P C Q P H L S F K V | SEQ ID NO: 48 |
| #2-12(111-130). | P C Q P H L S F K V D G T I V A Q P D P | SEQ ID NO: 49 |
| #2-13(121-140). | D G T I V A Q P D P A R W K N S K I W L | SEQ ID NO: 50 |
| #2-14(131-150). | A R W K N S K I W L Q F A Q L T D F N L | SEQ ID NO: 51 |
| #2-15(141-160). | Q F A Q L T D F N L M G T G V I D G Q G | SEQ ID NO: 52 |
| #2-16(151-170). | M G T G V I D G Q G Q Q W W A G Q C K V | SEQ ID NO: 53 |
| #2-17(161-180). | Q Q W W A G Q C K V V N G R T V C N D R | SEQ ID NO: 54 |
| #2-18(171-190). | V N G R T V C N D R N R P T A I K I D Y | SEQ ID NO: 55 |
| #2-19(181-200). | N R P T A I K I D Y S K S V T V K E L T | SEQ ID NO: 56 |
| #2-20(191-210). | S K S V T V K E L T L M N S P E F H L V | SEQ ID NO: 57 |
| #2-21(201-220). | L M N S P E F H L V F G E C E G V K I Q | SEQ ID NO: 58 |
| #2-22(211-230). | F G E C E G V K I Q G L K I K A P R D S | SEQ ID NO: 59 |
| #2-23(221-240). | G L K I K A P R D S P N T D G I D I F A | SEQ ID NO: 60 |
| #2-24(231-250). | P N T D G I D I F A S K R F H I E K C V | SEQ ID NO: 61 |
| #2-25(241-260). | S K R F H I E K C V I G T G D D C I A I | SEQ ID NO: 62 |
| #2-26(251-270). | I G T G D D C I A I G T G S S N I T I K | SEQ ID NO: 63 |
| #2-27(261-280). | G T G S S N I T I K D L I C G P G H G I | SEQ ID NO: 64 |

FIG. 6

2-28(271-290).D L I C G P G H G I S I G S L G R D N S SEQ ID NO: 65
2-29(281-300).S I G S L G R D N S R A E V S H V H V N SEQ ID NO: 66
2-30(291-310).R A E V S H V H V N R A K F I D T Q N G SEQ ID NO: 67
2-31(301-320).R A K F I D T Q N G L R I K T W Q G G S SEQ ID NO: 68
2-32(311-330).L R I K T W Q G G S G L A S Y I T Y E N SEQ ID NO: 69
2-33(321-340).G L A S Y I T Y E N V E M I N S E N P I SEQ ID NO: 70
2-34(331-350).V E M I N S E N P I L I N Q F Y C T S A SEQ ID NO: 71
2-35(341-360).L I N Q F Y C T S A S A C Q N Q R S A V SEQ ID NO: 72
2-36(351-370).S A C Q N Q R S A V Q I Q G V T Y K N I SEQ ID NO: 73
2-37(361-380).Q I Q G V T Y K N I H G T S A T A A A I SEQ ID NO: 74
2-38(371-390).H G T S A T A A A I Q L M C S D S V P C SEQ ID NO: 75
2-39(381-400).Q L M C S D S V P C T G I Q L S N V S L SEQ ID NO: 76
2-40(391-410).T G I Q L S N V S L K L T S G K P A S C SEQ ID NO: 77
2-41(401-420).K L T S G K P A S C V D K N A R G F Y S SEQ ID NO: 78
2-42(411-430).V D K N A R G F Y S G R L I P T C K N L SEQ ID NO: 79
2-43(421-440).G R L I P T C K N L R P G P S P K E F E SEQ ID NO: 80
2-44(431-450).R P G P S P K E F E L Q Q Q P T T V M D SEQ ID NO: 81
2-45(441-460).L Q Q Q P T T V M D E N K G A C A K G D SEQ ID NO: 82
2-46(451-470).E N K G A C A K G D S T C I S L S S S P SEQ ID NO: 83
2-47(461-480).S T C I S L S S S P P N C K N K C K G C SEQ ID NO: 84
2-48(471-490).P N C K N K C K G C Q P C K P K L L I V SEQ ID NO: 85
2-49(481-500).Q P C K P K L I I V H P N K P Q D Y Y P SEQ ID NO: 86
2-50(491-510).H P N K P Q D Y Y P Q K W V C S C H N K SEQ ID NO: 87
2-51(501-514).Q K W V C S C H N K I Y N P SEQ ID NO: 88

FIG. 7

| | | |
|---|---|---|
| #2-5(41-60). | S N R S L K K L V H S R H D A A T V F N | SEQ ID NO: 42 |
| #2-7(61-80). | V E Q Y G A V G D G K H D S T E A F A T | SEQ ID NO: 44 |
| #2-8(71-90). | K H D S T E A F A T T W N A A C K K A S | SEQ ID NO: 45 |
| #2-9(81-100). | T W N A A C K K A S A V L L V P A N K K | SEQ ID NO: 46 |
| #2-10(91-110). | A V L L V P A N K K F F V N N L V F R G | SEQ ID NO: 47 |
| #2-11(101-120). | F F V N N L V F R G P C Q P H L S F K V | SEQ ID NO: 48 |
| #2-12(111-130). | P C Q P H L S F K V D G T I V A Q P D P | SEQ ID NO: 49 |
| #2-13(121-140). | D G T I V A Q P D P A R W K N S K I W L | SEQ ID NO: 50 |
| #2-14(131-150). | A R W K N S K I W L Q F A Q L T D F N L | SEQ ID NO: 51 |
| #2-15(141-160). | Q F A Q L T D F N L M G T G V I D G Q G | SEQ ID NO: 52 |
| #2-16(151-170). | M G T G V I D G Q G Q Q W W A G Q C K V | SEQ ID NO: 53 |
| #2-17(161-180). | Q Q W W A G Q C K V V N G R T V C N D R | SEQ ID NO: 54 |
| #2-18(171-190). | V N G R T V C N D R N R P T A I K I D Y | SEQ ID NO: 55 |
| #2-19(181-200). | N R P T A I K I D Y S K S V T V K E L T | SEQ ID NO: 56 |
| #2-20(191-210). | S K S V T V K E L T L M N S P E F H L V | SEQ ID NO: 57 |
| #2-21(201-220). | L M N S P E P H L V F G E C E G V K I Q | SEQ ID NO: 58 |
| #2-22(211-230). | F G E C E G V K I Q G L K I K A P R D S | SEQ ID NO: 59 |
| #2-23(221-240). | G L K I K A P R D S P N T D G I D I F A | SEQ ID NO: 60 |
| #2-24(231-250). | P N T D G I D I F A S K R F H I E K C V | SEQ ID NO: 61 |
| #2-25(241-260). | S K R F H I E K C V I G T G D D C I A I | SEQ ID NO: 62 |
| #2-26(251-270). | I G T G D D C I A I G T G S S N I T I K | SEQ ID NO: 63 |
| #2-27(261-280). | G T G S S N I T I K D L I C G P G K G I | SEQ ID NO: 64 |
| #2-30(291-310). | R A E V S H V H V N R A K F I D T Q N G | SEQ ID NO: 67 |
| #2-31(301-320). | R A K F I D T Q N G L R I K T W Q G G S | SEQ ID NO: 68 |
| #2-32(311-330). | L R I K T W Q G G S G L A S Y I T Y E N | SEQ ID NO: 69 |
| #2-33(321-340). | G L A S Y I T Y E N V E M I N S E N P I | SEQ ID NO: 70 |
| #2-34(331-350). | V E M I N S E N P I L I N Q F Y C T S A | SEQ ID NO: 71 |
| #2-35(341-360). | L I N Q F Y C T S A S A C Q N Q R S A V | SEQ ID NO: 72 |
| #2-36(351-370). | S A C Q N Q R S A V Q I Q G V T Y K N I | SEQ ID NO: 73 |
| #2-37(361-380). | Q I Q G V T Y K N I H G T S A T A A A I | SEQ ID NO: 74 |
| #2-38(371-390). | H G T S A T A A A I Q L M C S D S V P C | SEQ ID NO: 75 |
| #2-40(391-410). | T G I Q L S N V S L K L T S G K P A S C | SEQ ID NO: 77 |
| #2-41(401-420). | K L T S G K P A S C V D K N A R G F Y S | SEQ ID NO: 78 |
| #2-42(411-430). | V D K N A R G F Y S G R L I P T C K N L | SEQ ID NO: 79 |
| #2-43(421-440). | G R L I P T C K N L R P G P S P K E F E | SEQ ID NO: 80 |

FIG. 8

2

SEQUENCE LISTING (1) GENERAL INFORMATION:

(iii) NUMBER OF SEQUENCES: 90

(2) INFORMATION FOR SEQ ID NO: 1:

(i) SEQUENCE CHARACTERISTICS:
       (A) LENGTH: 354 amino acids
       (B) TYPE: amino acid
       (D) TOPOLOGY: linear (ii) MOLECULE TYPE: protein (xi) SEQUENCE DESCRIPTION: SEQ ID NO: 1:

```
Asp Asn Pro Ile Asp Ser Cys Trp Arg Gly Asp Ala Asn Trp Asp Gln
 1               5                  10                  15

Asn Arg Met Lys Leu Ala Asp Cys Ala Val Gly Phe Gly Ser Ser Ala
                20                  25                  30

Met Gly Gly Lys Gly Gly Ala Phe Tyr Thr Val Thr Ser Ser Asp Asp
            35                  40                  45

Asp Pro Val Asn Pro Ala Pro Gly Thr Leu Arg Tyr Gly Ala Thr Arg
        50                  55                  60

Glu Arg Ser Leu Trp Ile Ile Phe Ser Lys Asn Leu Asn Ile Lys Leu
65                  70                  75                  80

Asn Met Pro Leu Tyr Ile Ala Gly Asn Lys Thr Ile Asp Gly Arg Gly
                85                  90                  95
```

```
Ala Glu Val His Ile Gly Asn Gly Gly Pro Cys Leu Phe Met Arg Thr
            100                 105                 110

Val Ser His Val Ile Leu His Gly Leu Asn Ile His Gly Cys Asn Thr
            115                 120                 125

Ser Val Ser Gly Asn Val Leu Ile Ser Glu Ala Ser Gly Val Val Pro
            130                 135                 140

Val His Ala Gln Asp Gly Asp Ala Ile Thr Met Arg Asn Val Thr Asp
145                 150                 155                 160

Val Trp Ile Asp His Asn Ser Leu Ser Asp Ser Asp Gly Leu Val
                165                 170                 175

Asp Val Thr Leu Ala Ser Thr Gly Val Thr Ile Ser Asn Asn His Phe
            180                 185                 190

Phe Asn His His Lys Val Met Leu Leu Gly His Ser Asp Ile Tyr Ser
            195                 200                 205

Asp Asp Lys Ser Met Lys Val Thr Val Ala Phe Asn Gln Phe Gly Pro
            210                 215                 220

Asn Ala Gly Gln Arg Met Pro Arg Ala Arg Tyr Gly Leu Ile His Val
225                 230                 235                 240

Ala Asn Asn Tyr Asp Pro Trp Ser Ile Tyr Ala Ile Gly Gly Ser
                245                 250                 255

Ser Asn Pro Thr Ile Leu Ser Glu Gly Asn Ser Phe Thr Ala Pro Asn
            260                 265                 270

Asp Ser Asp Lys Lys Glu Val Thr Arg Arg Val Gly Cys Glu Ser Pro
            275                 280                 285

Ser Thr Cys Ala Asn Trp Val Trp Arg Ser Thr Gln Asp Ser Phe Asn
            290                 295                 300

Asn Gly Ala Tyr Phe Val Ser Ser Gly Lys Asn Glu Gly Thr Asn Ile
305                 310                 315                 320

Tyr Asn Asn Asn Glu Ala Phe Lys Val Glu Asn Gly Ser Ala Ala Pro
                325                 330                 335

Gln Leu Thr Lys Asn Ala Gly Val Leu Thr Cys Ile Leu Ser Lys Pro
            340                 345                 350

Cys Ser (2) INFORMATION FOR SEQ ID NO: 2:

(i) SEQUENCE CHARACTERISTICS:
        (A) LENGTH: 514 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly Met Lys Phe Met Ala Ala Val Ala Phe Leu Ala Leu Gln Leu
1               5                   10                  15

Ile Val Met Ala Ala Ala Glu Asp Gln Ser Ala Gln Ile Met Leu Asp
                20                  25                  30

Ser Asp Ile Glu Gln Tyr Leu Arg Ser Asn Arg Ser Leu Lys Lys Leu
            35                  40                  45

Val His Ser Arg His Asp Ala Ala Thr Val Phe Asn Val Glu Gln Tyr
        50                  55                  60

Gly Ala Val Gly Asp Gly Lys His Asp Ser Thr Glu Ala Phe Ala Thr
65                  70                  75                  80

Thr Trp Asn Ala Ala Cys Lys Lys Ala Ser Ala Val Leu Leu Val Pro
```

-continued

```
                 85                  90                  95
Ala Asn Lys Lys Phe Phe Val Asn Asn Leu Val Phe Arg Gly Pro Cys
            100                 105                 110
Gln Pro His Leu Ser Phe Lys Val Asp Gly Thr Ile Val Ala Gln Pro
            115                 120                 125
Asp Pro Ala Arg Trp Lys Asn Ser Lys Ile Trp Leu Gln Phe Ala Gln
            130                 135                 140
Leu Thr Asp Phe Asn Leu Met Gly Thr Gly Val Ile Asp Gly Gln Gly
145                 150                 155                 160
Gln Gln Trp Trp Ala Gly Gln Cys Lys Val Val Asn Gly Arg Thr Val
                165                 170                 175
Cys Asn Asp Arg Asn Arg Pro Thr Ala Ile Lys Ile Asp Tyr Ser Lys
            180                 185                 190
Ser Val Thr Val Lys Glu Leu Thr Leu Met Asn Ser Pro Glu Phe His
            195                 200                 205
Leu Val Phe Gly Glu Cys Glu Gly Val Lys Ile Gln Gly Leu Lys Ile
            210                 215                 220
Lys Ala Pro Arg Asp Ser Pro Asn Thr Asp Gly Ile Asp Ile Phe Ala
225                 230                 235                 240
Ser Lys Arg Phe His Ile Glu Lys Cys Val Ile Gly Thr Gly Asp Asp
                245                 250                 255
Cys Ile Ala Ile Gly Thr Gly Ser Ser Asn Ile Thr Ile Lys Asp Leu
            260                 265                 270
Ile Cys Gly Pro Gly His Gly Ile Ser Ile Gly Ser Leu Gly Arg Asp
            275                 280                 285
Asn Ser Arg Ala Glu Val Ser His Val His Val Asn Arg Ala Lys Phe
            290                 295                 300
Ile Asp Thr Gln Asn Gly Leu Arg Ile Lys Thr Trp Gln Gly Gly Ser
305                 310                 315                 320
Gly Leu Ala Ser Tyr Ile Thr Tyr Glu Asn Val Glu Met Ile Asn Ser
                325                 330                 335
Glu Asn Pro Ile Leu Ile Asn Gln Phe Tyr Cys Thr Ser Ala Ser Ala
            340                 345                 350
Cys Gln Asn Gln Arg Ser Ala Val Gln Ile Gln Gly Val Thr Tyr Lys
            355                 360                 365
Asn Ile His Gly Thr Ser Ala Thr Ala Ala Ile Gln Leu Met Cys
            370                 375                 380
Ser Asp Ser Val Pro Cys Thr Gly Ile Gln Leu Ser Asn Val Ser Leu
385                 390                 395                 400
Lys Leu Thr Ser Gly Lys Pro Ala Ser Cys Val Asp Lys Asn Ala Arg
                405                 410                 415
Gly Phe Tyr Ser Gly Arg Leu Ile Pro Thr Cys Lys Asn Leu Arg Pro
                420                 425                 430
Gly Pro Ser Pro Lys Glu Phe Glu Leu Gln Gln Pro Thr Thr Val
            435                 440                 445
Met Asp Glu Asn Lys Gly Ala Cys Ala Lys Gly Asp Ser Thr Cys Ile
            450                 455                 460
Ser Leu Ser Ser Pro Pro Asn Cys Lys Asn Lys Cys Lys Gly Cys
465                 470                 475                 480
Gln Pro Cys Lys Pro Lys Leu Ile Ile Val His Pro Asn Lys Pro Gln
                485                 490                 495
Asp Tyr Tyr Pro Gln Lys Trp Val Cys Ser Cys His Asn Lys Ile Tyr
            500                 505                 510
```

```
Asn Pro (2) INFORMATION FOR SEQ ID NO: 3:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 3:

Asp Asn Pro Ile Asp Ser Cys Trp Arg Gly Asp Ala Asn Trp Asp Gln
  1               5                  10                  15

Asn Arg Met Lys
            20

(2) INFORMATION FOR SEQ ID NO: 4:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 4:

Asp Ala Asn Trp Asp Gln Asn Arg Met Lys Leu Ala Asp Cys Ala Val
  1               5                  10                  15

Gly Phe Gly Ser
            20

(2) INFORMATION FOR SEQ ID NO: 5:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 5:

Leu Ala Asp Cys Ala Val Gly Phe Gly Ser Ser Ala Met Gly Gly Lys
  1               5                  10                  15

Gly Gly Ala Phe
            20

(2) INFORMATION FOR SEQ ID NO: 6:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 6:

Ser Ala Met Gly Gly Lys Gly Gly Ala Phe Tyr Thr Val Thr Ser Ser
  1               5                  10                  15

Asp Asp Pro
        20

(2) INFORMATION FOR SEQ ID NO: 7:

(i) SEQUENCE CHARACTERISTICS:
```

(A) LENGTH: 20 amino acids
    (B) TYPE: amino acid
    (D) TOPOLOGY: linear (ii) MOLECULE TYPE: protein (xi) SEQUENCE DESCRIPTION: SEQ ID NO: 7:

Tyr Thr Val Thr Ser Ser Asp Asp Pro Val Asn Pro Ala Pro Gly
 1               5                  10                  15

Thr Leu Arg Tyr
            20

(2) INFORMATION FOR SEQ ID NO: 8:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 8:

Val Asn Pro Ala Pro Gly Thr Leu Arg Tyr Gly Ala Thr Arg Glu Arg
 1               5                  10                  15

Ser Leu Trp Ile
            20

(2) INFORMATION FOR SEQ ID NO: 9:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 9:

Gly Ala Thr Arg Glu Arg Ser Leu Trp Ile Ile Phe Ser Lys Asn Leu
 1               5                  10                  15

Asn Ile Lys Leu
            20

(2) INFORMATION FOR SEQ ID NO: 10:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 10:

Ile Phe Ser Lys Asn Leu Asn Ile Lys Leu Asn Met Pro Leu Tyr Ile
 1               5                  10                  15

Ala Gly Asn Lys
            20

(2) INFORMATION FOR SEQ ID NO: 11:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 11:

```
Asn Met Pro Leu Tyr Ile Ala Gly Asn Lys Thr Ile Asp Gly Arg Gly
  1               5                  10                  15

Ala Glu Val His
            20

(2) INFORMATION FOR SEQ ID NO: 12:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 12:

Thr Ile Asp Gly Arg Gly Ala Glu Val His Ile Gly Asn Gly Gly Pro
  1               5                  10                  15

Cys Leu Phe Met
            20

(2) INFORMATION FOR SEQ ID NO: 13:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 13:

Ile Gly Asn Gly Gly Pro Cys Leu Phe Met Arg Thr Val Ser His Val
  1               5                  10                  15

Ile Leu His Gly
            20

(2) INFORMATION FOR SEQ ID NO: 14:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 14:

Arg Thr Val Ser His Val Ile Leu His Gly Leu Asn Ile His Gly Cys
  1               5                  10                  15

Asn Thr Ser Val
            20

(2) INFORMATION FOR SEQ ID NO: 15:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 15:

Leu Asn Ile His Gly Cys Asn Thr Ser Val Ser Gly Asn Val Leu Ile
  1               5                  10                  15

Ser Glu Ala Ser
            20
```

(2) INFORMATION FOR SEQ ID NO: 16:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 16:

Ser Gly Asn Val Leu Ile Ser Glu Ala Ser Gly Val Val Pro Val His
 1               5                  10                  15

Ala Gln Asp Gly
            20

(2) INFORMATION FOR SEQ ID NO: 17:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 17:

Gly Val Val Pro Val His Ala Gln Asp Gly Asp Ala Ile Thr Met Arg
 1               5                  10                  15

Asn Val Thr Asp
            20

(2) INFORMATION FOR SEQ ID NO: 18:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 18:

Asp Ala Ile Thr Met Arg Asn Val Thr Asp Val Trp Ile Asp His Asn
 1               5                  10                  15

Ser Leu Ser Asp
            20

(2) INFORMATION FOR SEQ ID NO: 19:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 19:

Val Trp Ile Asp His Asn Ser Leu Ser Asp Ser Ser Asp Gly Leu Val
 1               5                  10                  15

Asp Val Thr Leu
            20

(2) INFORMATION FOR SEQ ID NO: 20:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 20:

Ser Ser Asp Gly Leu Val Asp Val Thr Leu Ala Ser Thr Gly Val Thr
1               5                   10                  15

Ile Ser Asn Asn
            20

(2) INFORMATION FOR SEQ ID NO: 21:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO: 21:

Ala Ser Thr Gly Val Thr Ile Ser Asn Asn His Phe Phe Asn His His
1               5                   10                  15

Lys Val Met Leu
            20

(2) INFORMATION FOR SEQ ID NO: 22:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO: 22:

His Phe Phe Asn His His Lys Val Met Leu Leu Gly His Ser Asp Ile
1               5                   10                  15

Tyr Ser Asp Asp
            20

(2) INFORMATION FOR SEQ ID NO: 23:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (xi) SEQUENCE DESCRIPTION: SEQ ID NO: 23:

Leu Gly His Ser Asp Ile Tyr Ser Asp Asp Lys Ser Met Lys Val Thr
1               5                   10                  15

Val Ala Phe Asn
            20

(2) INFORMATION FOR SEQ ID NO: 24:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO: 24:

Lys Ser Met Lys Val Thr Val Ala Phe Asn Gln Phe Gly Pro Asn Ala
1               5                   10                  15

```
Gly Gln Arg Met
        20

(2) INFORMATION FOR SEQ ID NO: 25:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 25:

Gln Phe Gly Pro Asn Ala Gly Gln Arg Met Pro Arg Ala Arg Tyr Gly
 1               5                  10                  15

Leu Ile His Val
        20

(2) INFORMATION FOR SEQ ID NO: 26:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 26:

Pro Arg Ala Arg Tyr Gly Leu Ile His Val Ala Asn Asn Asn Tyr Asp
 1               5                  10                  15

Pro Trp Ser Ile
        20

(2) INFORMATION FOR SEQ ID NO: 27:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 27:

Ala Asn Asn Asn Tyr Asp Pro Trp Ser Ile Tyr Ala Ile Gly Gly Ser
 1               5                  10                  15

Ser Asn Pro Thr
        20

(2) INFORMATION FOR SEQ ID NO: 28:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 28:

Tyr Ala Ile Gly Gly Ser Ser Asn Pro Thr Ile Leu Ser Glu Gly Asn
 1               5                  10                  15

Ser Phe Thr Ala
        20

(2) INFORMATION FOR SEQ ID NO: 29:
```

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 29:

Ile Leu Ser Glu Gly Asn Ser Phe Thr Ala Pro Asn Asp Ser Asp Lys
 1               5                  10                  15

Lys Glu Val Thr
            20

(2) INFORMATION FOR SEQ ID NO: 30:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 30:

Pro Asn Asp Ser Asp Lys Lys Glu Val Thr Arg Arg Val Gly Cys Glu
 1               5                  10                  15

Ser Pro Ser Thr
            20

(2) INFORMATION FOR SEQ ID NO: 31:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 31:

Arg Arg Val Gly Cys Glu Ser Pro Ser Thr Cys Ala Asn Trp Val Trp
 1               5                  10                  15

Arg Ser Thr Gln
            20

(2) INFORMATION FOR SEQ ID NO: 32:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 32:

Cys Ala Asn Trp Val Trp Arg Ser Thr Gln Asp Ser Phe Asn Asn Gly
 1               5                  10                  15

Ala Tyr Phe Val
            20

(2) INFORMATION FOR SEQ ID NO: 33:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 33:

Asp Ser Phe Asn Asn Gly Ala Tyr Phe Val Ser Ser Gly Lys Asn Glu
 1               5                  10                  15

Gly Thr Asn Ile
            20

(2) INFORMATION FOR SEQ ID NO: 34:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 34:

Ser Ser Gly Lys Asn Glu Gly Thr Asn Ile Tyr Asn Asn Asn Glu Ala
 1               5                  10                  15

Phe Lys Val Glu
            20

(2) INFORMATION FOR SEQ ID NO: 35:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 35:

Tyr Asn Asn Asn Glu Ala Phe Lys Val Glu Asn Gly Ser Ala Ala Pro
 1               5                  10                  15

Gln Leu Thr Lys
            20

(2) INFORMATION FOR SEQ ID NO: 36:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 36:

Asn Gly Ser Ala Ala Pro Gln Leu Thr Lys Asn Ala Gly Val Leu Thr
 1               5                  10                  15

Cys Ile Leu Ser
            20

(2) INFORMATION FOR SEQ ID NO: 37:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 37:

Asn Ala Gly Val Leu Thr Cys Ile Leu Ser Lys Pro Cys Ser
 1               5                  10

(2) INFORMATION FOR SEQ ID NO: 38:

```
    (i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 38:

Met Gly Met Lys Phe Met Ala Ala Val Ala Phe Leu Ala Leu Gln Leu
 1               5                  10                  15

Ile Val Met Ala
            20

(2) INFORMATION FOR SEQ ID NO: 39:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 39:

Phe Leu Ala Leu Gln Leu Ile Val Met Ala Ala Ala Glu Asp Gln Ser
 1               5                  10                  15

Ala Gln Ile Met
            20

(2) INFORMATION FOR SEQ ID NO: 40:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 40:

Ala Ala Glu Asp Gln Ser Ala Gln Ile Met Leu Asp Ser Asp Ile Glu
 1               5                  10                  15

Gln Tyr Leu Arg
            20

(2) INFORMATION FOR SEQ ID NO: 41:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 41:

Leu Asp Ser Asp Ile Glu Gln Tyr Leu Arg Ser Asn Arg Ser Leu Lys
 1               5                  10                  15

Lys Leu Val His
            20

(2) INFORMATION FOR SEQ ID NO: 42:

(i) SEQUENCE CHARACTERISTICS:
        (A) LENGTH: 20 amino acids
        (B) TYPE: amino acid
        (D) TOPOLOGY: linear (ii) MOLECULE TYPE: protein
```

(xi) SEQUENCE DESCRIPTION: SEQ ID NO: 42:

Ser Asn Arg Ser Leu Lys Lys Leu Val His Ser Arg His Asp Ala Ala
1               5                   10                  15

Thr Val Phe Asn
            20

(2) INFORMATION FOR SEQ ID NO: 43:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 43:

Ser Arg His Asp Ala Ala Thr Val Phe Asn Val Glu Gln Tyr Gly Ala
1               5                   10                  15

Val Gly Asp Gly
            20

(2) INFORMATION FOR SEQ ID NO: 44:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 44:

Val Glu Gln Tyr Gly Ala Val Gly Asp Gly Lys His Asp Ser Thr Glu
1               5                   10                  15

Ala Phe Ala Thr
            20

(2) INFORMATION FOR SEQ ID NO: 45:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 45:

Lys His Asp Ser Thr Glu Ala Phe Ala Thr Thr Trp Asn Ala Ala Cys
1               5                   10                  15

Lys Lys Ala Ser
            20

(2) INFORMATION FOR SEQ ID NO: 46:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 46:

Thr Trp Asn Ala Ala Cys Lys Lys Ala Ser Ala Val Leu Leu Val Pro
1               5                   10                  15

Ala Asn Lys Lys (2) INFORMATION FOR SEQ ID NO: 47:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 47:

Ala Val Leu Leu Val Pro Ala Asn Lys Lys Phe Phe Val Asn Asn Leu
 1               5                  10                  15

Val Phe Arg Gly
            20

(2) INFORMATION FOR SEQ ID NO: 48:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 48:

Phe Phe Val Asn Asn Leu Val Phe Arg Gly Pro Cys Gln Pro His Leu
 1               5                  10                  15

Ser Phe Lys Val
            20

(2) INFORMATION FOR SEQ ID NO: 49:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 49:

Pro Cys Gln Pro His Leu Ser Phe Lys Val Asp Gly Thr Ile Val Ala
 1               5                  10                  15

Gln Pro Asp Pro
            20

(2) INFORMATION FOR SEQ ID NO: 50:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 50:

Asp Gly Thr Ile Val Ala Gln Pro Asp Pro Ala Arg Trp Lys Asn Ser
 1               5                  10                  15

Lys Ile Trp Leu
            20

(2) INFORMATION FOR SEQ ID NO: 51:

(i) SEQUENCE CHARACTERISTICS:
        (A) LENGTH: 20 amino acids

```
            (B) TYPE: amino acid
            (D) TOPOLOGY: linear (ii) MOLECULE TYPE: protein (xi) SEQUENCE DESCRIPTION: SEQ ID NO: 51:

Ala Arg Trp Lys Asn Ser Lys Ile Trp Leu Gln Phe Ala Gln Leu Thr
 1               5                  10                  15

Asp Phe Asn Leu
            20

(2) INFORMATION FOR SEQ ID NO: 52:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO: 52:

Gln Phe Ala Gln Leu Thr Asp Phe Asn Leu Met Gly Thr Gly Val Ile
 1               5                  10                  15

Asp Gly Gln Gly
            20

(2) INFORMATION FOR SEQ ID NO: 53:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO: 53:

Met Gly Thr Gly Val Ile Asp Gly Gln Gly Gln Gln Trp Trp Ala Gly
 1               5                  10                  15

Gln Cys Lys Val
            20

(2) INFORMATION FOR SEQ ID NO: 54:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO: 54:

Gln Gln Trp Trp Ala Gly Gln Cys Lys Val Val Asn Gly Arg Thr Val
 1               5                  10                  15

Cys Asn Asp Arg
            20

(2) INFORMATION FOR SEQ ID NO: 55:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO: 55:
```

-continued

```
Val Asn Gly Arg Thr Val Cys Asn Asp Arg Asn Arg Pro Thr Ala Ile
 1               5                  10                  15
Lys Ile Asp Tyr
            20

(2) INFORMATION FOR SEQ ID NO: 56:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 56:

Asn Arg Pro Thr Ala Ile Lys Ile Asp Tyr Ser Lys Ser Val Thr Val
 1               5                  10                  15
Lys Glu Leu Thr
            20

(2) INFORMATION FOR SEQ ID NO: 57:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 57:

Ser Lys Ser Val Thr Val Lys Glu Leu Thr Leu Met Asn Ser Pro Glu
 1               5                  10                  15
Phe His Leu Val
            20

(2) INFORMATION FOR SEQ ID NO: 58:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 58:

Leu Met Asn Ser Pro Glu Phe His Leu Val Phe Gly Glu Cys Glu Gly
 1               5                  10                  15
Val Lys Ile Gln
            20

(2) INFORMATION FOR SEQ ID NO: 59:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 59:

Phe Gly Glu Cys Glu Gly Val Lys Ile Gln Gly Leu Lys Ile Lys Ala
 1               5                  10                  15
Pro Arg Asp Ser
            20
```

(2) INFORMATION FOR SEQ ID NO: 60:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 60:

```
Gly Leu Lys Ile Lys Ala Pro Arg Asp Ser Pro Asn Thr Asp Gly Ile
 1               5                  10                  15

Asp Ile Phe Ala
            20
```

(2) INFORMATION FOR SEQ ID NO: 61:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 61:

```
Pro Asn Thr Asp Gly Ile Asp Ile Phe Ala Ser Lys Arg Phe His Ile
 1               5                  10                  15

Glu Lys Cys Val
            20
```

(2) INFORMATION FOR SEQ ID NO: 62:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 62:

```
Ser Lys Arg Phe His Ile Glu Lys Cys Val Ile Gly Thr Gly Asp Asp
 1               5                  10                  15

Cys Ile Ala Ile
            20
```

(2) INFORMATION FOR SEQ ID NO: 63:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 63:

```
Ile Gly Thr Gly Asp Asp Cys Ile Ala Ile Gly Thr Gly Ser Ser Asn
 1               5                  10                  15

Ile Thr Ile Lys
            20
```

(2) INFORMATION FOR SEQ ID NO: 64:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 64:

Gly Thr Gly Ser Ser Asn Ile Thr Ile Lys Asp Leu Ile Cys Gly Pro
 1               5                  10                  15

Gly His Gly Ile
            20

(2) INFORMATION FOR SEQ ID NO: 65:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 65:

Asp Leu Ile Cys Gly Pro Gly His Gly Ile Ser Ile Gly Ser Leu Gly
 1               5                  10                  15

Arg Asp Asn Ser
            20

(2) INFORMATION FOR SEQ ID NO: 66:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 66:

Ser Ile Gly Ser Leu Gly Arg Asp Asn Ser Arg Ala Glu Val Ser His
 1               5                  10                  15

Val His Val Asn
            20

(2) INFORMATION FOR SEQ ID NO: 67:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 67:

Arg Ala Glu Val Ser His Val His Val Asn Arg Ala Lys Phe Ile Asp
 1               5                  10                  15

Thr Gln Asn Gly
            20

(2) INFORMATION FOR SEQ ID NO: 68:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 68:

Arg Ala Lys Phe Ile Asp Thr Gln Asn Gly Leu Arg Ile Lys Thr Trp
 1               5                  10                  15

```
Gln Gly Gly Ser
            20

(2) INFORMATION FOR SEQ ID NO: 69:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 69:

Leu Arg Ile Lys Thr Trp Gln Gly Gly Ser Gly Leu Ala Ser Tyr Ile
  1               5                  10                  15

Thr Tyr Glu Asn
            20

(2) INFORMATION FOR SEQ ID NO: 70:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 70:

Gly Leu Ala Ser Tyr Ile Thr Tyr Glu Asn Val Glu Met Ile Asn Ser
  1               5                  10                  15

Glu Asn Pro Ile
            20

(2) INFORMATION FOR SEQ ID NO: 71:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 71:

Val Glu Met Ile Asn Ser Glu Asn Pro Ile Leu Ile Asn Gln Phe Tyr
  1               5                  10                  15

Cys Thr Ser Ala
            20

(2) INFORMATION FOR SEQ ID NO: 72:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 72:

Leu Ile Asn Gln Phe Tyr Cys Thr Ser Ala Ser Ala Cys Gln Asn Gln
  1               5                  10                  15

Arg Ser Ala Val
            20

(2) INFORMATION FOR SEQ ID NO: 73:

(i) SEQUENCE CHARACTERISTICS:
```

(A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 73:

Ser Ala Cys Gln Asn Gln Arg Ser Ala Val Gln Ile Gln Gly Val Thr
 1               5                  10                  15

Tyr Lys Asn Ile
            20

(2) INFORMATION FOR SEQ ID NO: 74:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 74:

Gln Ile Gln Gly Val Thr Tyr Lys Asn Ile His Gly Thr Ser Ala Thr
 1               5                  10                  15

Ala Ala Ala Ile
            20

(2) INFORMATION FOR SEQ ID NO: 75:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 75:

His Gly Thr Ser Ala Thr Ala Ala Ala Ile Gln Leu Met Cys Ser Asp
 1               5                  10                  15

Ser Val Pro Cys
            20

(2) INFORMATION FOR SEQ ID NO: 76:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 76:

Gln Leu Met Cys Ser Asp Ser Val Pro Cys Thr Gly Ile Gln Leu Ser
 1               5                  10                  15

Asn Val Ser Leu
            20

(2) INFORMATION FOR SEQ ID NO: 77:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 77:

```
Thr Gly Ile Gln Leu Ser Asn Val Ser Leu Lys Leu Thr Ser Gly Lys
  1               5                  10                  15

Pro Ala Ser Cys
            20

(2) INFORMATION FOR SEQ ID NO: 78:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 78:

Lys Leu Thr Ser Gly Lys Pro Ala Ser Cys Val Asp Lys Asn Ala Arg
  1               5                  10                  15

Gly Phe Tyr Ser
            20

(2) INFORMATION FOR SEQ ID NO: 79:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 79:

Val Asp Lys Asn Ala Arg Gly Phe Tyr Ser Gly Arg Leu Ile Pro Thr
  1               5                  10                  15

Cys Lys Asn Leu
            20

(2) INFORMATION FOR SEQ ID NO: 80:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 80:

Gly Arg Leu Ile Pro Thr Cys Lys Asn Leu Arg Pro Gly Pro Ser Pro
  1               5                  10                  15

Lys Glu Phe Glu
            20

(2) INFORMATION FOR SEQ ID NO: 81:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 81:

Arg Pro Gly Pro Ser Pro Lys Glu Phe Glu Leu Gln Gln Gln Pro Thr
  1               5                  10                  15

Thr Val Met Asp
            20
```

(2) INFORMATION FOR SEQ ID NO: 82:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 82:

Leu Gln Gln Gln Pro Thr Thr Val Met Asp Glu Asn Lys Gly Ala Cys
  1               5                  10                  15

Ala Lys Gly Asp
            20

(2) INFORMATION FOR SEQ ID NO: 83:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 83:

Glu Asn Lys Gly Ala Cys Ala Lys Gly Asp Ser Thr Cys Ile Ser Leu
  1               5                  10                  15

Ser Ser Ser Pro
            20

(2) INFORMATION FOR SEQ ID NO: 84:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 84:

Ser Thr Cys Ile Ser Leu Ser Ser Ser Pro Pro Asn Cys Lys Asn Lys
  1               5                  10                  15

Cys Lys Gly Cys
            20

(2) INFORMATION FOR SEQ ID NO: 85:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 85:

Pro Asn Cys Lys Asn Lys Cys Lys Gly Cys Gln Pro Cys Lys Pro Lys
  1               5                  10                  15

Leu Ile Ile Val
            20

(2) INFORMATION FOR SEQ ID NO: 86:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 86:

Gln Pro Cys Lys Pro Lys Leu Ile Ile Val His Pro Asn Lys Pro Gln
  1               5                  10                  15

Asp Tyr Tyr Pro
             20

(2) INFORMATION FOR SEQ ID NO: 87:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO: 87:

His Pro Asn Lys Pro Gln Asp Tyr Tyr Pro Gln Lys Trp Val Cys Ser
  1               5                  10                  15

Cys His Asn Lys
             20

(2) INFORMATION FOR SEQ ID NO: 88:

(i) SEQUENCE CHARACTERISTICS:
            (A) LENGTH: 14 amino acids
            (B) TYPE: amino acid
            (D) TOPOLOGY: linear (ii) MOLECULE TYPE: protein (xi) SEQUENCE DESCRIPTION: SEQ ID NO: 88:

Gln Lys Trp Val Cys Ser Cys His Asn Lys Ile Tyr Asn Pro
  1               5                  10

(2) INFORMATION FOR SEQ ID NO: 89:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO: 89:

Phe Phe Val Asn Asn Leu Val Phe Arg Gly Pro Cys Gln Pro His Leu
  1               5                  10                  15

Pro Phe Lys Val
             20

(2) INFORMATION FOR SEQ ID NO: 90:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO: 90:

```
Pro Cys Gln Pro His Leu Pro Phe Lys Val Asp Gly Thr Ile Val Ala
  1               5                  10                 15

Gln Pro Asp Pro
           20
```

T-CELL EPITOPE PEPTIDES

This application is a divisional, and claims priority of U.S. application Ser. No. 11/354,543, filed Feb. 14, 2006, now U.S. Pat. No. 7,407,657, issued Aug. 5, 2008, which is a divisional of U.S. application Ser. No. 09/202,464, filed Mar. 9, 1999, now U.S. Pat. No. 7,112,329, issued Sep. 26, 2006, which claims priority of International Application No. PCT/JP97/02031, filed Jun. 12, 1997, which claims priority of Japanese Patent Application No.JP8/153527, filed Jun. 14, 1996. The disclosures of U.S. application Ser. Nos. 11/354,543 and 09/202,464, International Application No. PCT/JP97/02031, and Japanese Patent Application No. JP8/153527 are incorporated herein by reference in their entirety.

TECHNICAL FIELD

The present invention relates to T-cell epitope peptides of pollen allergen and a composition for peptide-based immunotherapy comprising the peptides as effective ingredients. This composition is useful for treating and/or preventing pollinosis in springtime.

BACKGROUND ART

About 10% of the Japanese population suffers from pollinosis developed in springtime such as cedar pollinosis. This condition has been on the increase and is attracting public attention.

The period when pollinosis is developed generally corresponds to the period when pollens scatter. In many cases, symptoms of pollinosis still remain after the season in which cedar pollens scatter because most patients with cedar pollinosis are also sensitized with Japanese cypress pollens (Hiroki cypress pollens) that start to scatter just after the cedar pollen-scattering period. Thus, patients who are also sensitive to Japanese cypress pollens suffer from the symptoms of pollinosis for a significant portion of the year.

Cedar pollens and Japanese cypress pollens possess common antigenicity (Takeshi Ide et al., Allergy Clinic 11, 174-178, 1991). The cross-reactivity of IgE antibodies between cedar pollens and Japanese cypress pollens has been established (Taniai M. et al., Mol. Immunol. 30, 183-189, 1993). The positivity index of patients with spring pollinosis for their allergen-specific IgE antibodies is 83.5% for cedar pollens, 80.0% for Japanese cypress pollens, and 76.4% for both pollens (Mitsuhiro Okano et al., Allergy 43, 1179-1184, 1994). In addition, 60% of the patients with cedar pollinosis possess Japanese cypress pollen-specific IgE antibodies (Yozo Saito, Chiryo (Therapy) 78, 1571-1576, 1996). Based on these reports, it is generally recognized that cedar pollinosis patients can develop pollinosis to Japanese cypress pollens and vice versa.

Pollinosis is a typical immediate type I allergy induced by an antigen-antibody reaction between a pollen allergen (which is an antigen causing allergy and is substantially the same as an antigen) and an IgE antibody specific to the allergen. Thus, pollinosis is now prevented and treated using methods theoretically based on the mechanism by which type I allergies develop. This mechanism is briefly described below.

An antigen that has invaded the body is presented to helper T cells by antigen-presenting cells. As a result, B cells mature into antibody-producing cells. The antibody-producing cells produce an antigen-specific IgE antibody, which binds to the surface of mast cells. A subsequently invading antigen binds to the IgE antibody on the mast cells. This stimulation releases chemical mediators like histamine from the mast cells, thereby causing an allergic symptom.

The following three methods are mainly used to prevent and treat allergies based on the above mechanism: 1) evasion of an antigen that causes allergy, 2) chemotherapy typically using an anti-histaminic, and 3) desensitization therapy using an allergen. However, method 1) is difficult to implement practically, and method 2) is merely symptomatic therapy. Method 3) is expected to be the only treatment attacking the root problem, but it is not always effective and may cause serious side effects such as anaphylactic shock.

For these reasons, peptide-based immunotherapy using T-cell epitope peptides of allergen has been recently attempted to prevent and treat allergies. T-cell epitopes participate in initiating and retaining an immune response to a protein allergen that causes clinical symptoms of allergies. These T-cell epitopes bind to HLA class. II molecules on the surface of antigen-presenting cells to stimulate the related T-cell subpopulation. The stimulation is thought to trigger an initial response at the helper T-cell level. This initial response causes proliferation of T cells, secretion of lymphokines, a localized inflammatory response, migration of proliferated immune cells to the inflammatory sites, and activation of the B-cell cascade that precedes antibody production. IgE antibodies that are isotypes of these antibodies are critical to the development and retention of allergies. Furthermore, their production is influenced by the properties of lymphokines secreted by helper T cells at the beginning of the above-described cascade. The T-cell epitope is a basic element or the minimum unit to be recognized by a T-cell receptor. This epitope contains amino acid sequence necessary to recognize the receptor. Allergic inflammation can be treated by controlling the response of the helper T cell, which plays a key role in immunosuppression, using the T-cell epitope peptide.

Known therapeutic agents for allergies using T-cell epitope peptides include a therapeutic composition comprising a T-cell epitope peptide of cat-origin allergen (a PCT application published in Japan (JP-WA) No. Hei 7-505365), a therapeutic composition comprising a T-cell epitope peptide of cedar pollen Cry j 1 (JP-WA-Hei 8-502163), and a multi-epitope peptide obtained by joining T-cell epitopes of cedar pollens Cry j 1 and Cry j 2 (Japanese Patent Application No. Hei 8-80702). The main allergen of Japanese cypress pollen, Cha o 1, is reported to have molecular weights of 45 KD or 50 KD. Each molecule has the same isoelectric point of 6.8 and consists of a protein containing 5% carbohydrate (Takeshi Ide, et al., Nippon Kafun Gakkaishi (Journal of the Japanese Pollen Association) 34, 39, 1988). However, their primary structures were unknown, and accordingly, no T-cell epitope site has been identified on the allergen molecules yet. Recently, the present inventors succeeded in cloning the Japanese cypress pollen allergen gene, and clarified that, in addition to Cha o 1, another type of the allergen, Cha o 2, was present. Furthermore, the primary structures of Cha o 1 and Cha o 2 were determined (Japanese Patent Application No. Hei 6-335089).

DISCLOSURE OF THE INVENTION

The period when cedar pollen scatter overlaps that of Japanese cypress pollen is referred to as the mixed pollen-scattering period. These two pollens possess a common antigenicity, which makes it difficult to distinguish symptoms caused by cedar pollens from those caused by Japanese cypress pollens. The symptoms sometimes continue or develop even after the cedar pollen-scattering period. Since pollens found in the air during that period are mostly Japanese cypress pollens, these symptoms seem to be caused by Japanese cypress pollens. Since more Japanese cypress trees are planted than cedar trees, the amount of scattered Japanese cypress pollen is increasing year after year and will exceed that of cedar pollens in the near future. It is thus desirable to establish a method for preventing and treating allergies based on the root overall pollinosis caused by tree pollens in springtime, including Japanese cypress pollinosis and cedar pollinosis. Peptide-based immunotherapy using T-cell epitope peptides is expected to lead to allergy treatment based on the root pollinosis. As described above, several methods for such immunotherapy are known for cedar pollinosis. However, nothing has been reported on Japanese cypress pollinosis or on pollinosis caused by tree pollens in springtime, including cedar and Japanese cypress pollens.

An objective of the present invention is to provide T-cell epitope peptides useful for peptide-based immunotherapy for Japanese cypress pollinosis. Another objective of the present invention is to provide T-cell epitope peptides useful for peptide-based immunotherapy for patients with pollinosis caused by tree pollens in springtime including patients with cedar pollinosis who show a cross-reactivity with Japanese cypress pollens.

The present inventors have identified a T-cell epitope site on the allergen molecules of Japanese cypress pollen by stimulating a T-cell line established from patients with Japanese cypress pollinosis with synthetic overlapping peptides that cover the entire primary structure of Japanese cypress pollen allergens, thus solving the above problems.

The present invention is comprised of the inventions described in each claim and will be described below in more detail.

The present inventors determined the amino acid sequence (described in Japanese Patent Application No. Hei 6-335089) of the major allergen, Cha o 1 (mature protein), of Japanese cypress pollen allergen shown as SEQ ID NO: 1 and that of Cha o 2 shown as SEQ ID NO: 2. The amino acid sequence of Cha o 1 has 80% homology to cedar pollen allergen Cry j 1, and that of Cha o 2 has 75% homology to cedar pollen allergen Cry j 2.

A number of amino acid substitutions are observed in the allergens derived from pollens, mites, and bee venom. These allergen species are called isoallergens. For example, eleven isoallergens have been isolated from birch tree pollen Bet v I, and their amino acid sequences differ from each other within a range of 2 to 15% (Swoboda, I. et al., J. Biol. Chem. 270: 2607-2613, 1995). At present, two isoallergens, in which six amino acid residues are substituted in a mature protein region, have been found in Cry j 2 (unexamined published Japanese Patent Applications (JP-A) No. Hei 8-47392 and No. Hei 7-170986). One skilled in the art can reasonably expect that isoallergens would be present in Cha o 1 and Cha o 2 as well. Such isoallergens are also included in Cha o 1 and Cha o 2 referred to in the present invention.

The family of cedar trees is classified into nine genera, and the family of Japanese cypress, into seven genera. It is reported that allergens from *Cryptomeria*, Redwood, and *Metasequoia*, which belong to the cedar (Taxodiaceae) family, and Umbrella Pine, which is hypothesized to belong to either an independent family, the cedar family, or the pine family, show cross-reactivity with those from Japanese Cypress, Sawara Cypress, Oriental Arbor-vitae, Needle Junipers and Chinese Juniper, which belong to the family of Cupressaceae (Takeshi Ide, et al., Allergy Clinic, 11, 174-178, 1991). In view of this report, cedar allergens are broadly cross-reactive with the allergens of Japanese cypress. Therefore, the peptides of the present invention are generally effective not only for Japanese cypress pollinosis but also for cedar pollinosis as well.

To obtain the T-cell epitope peptides of the present invention, overlapping peptides that cover the entire primary structures of Cha o 1 and Cha o 2 were synthesized; each peptide consists of the adequate number of amino acid residues (12 to 20 residues). The peptide of the present invention stimulates and/or suppresses the activity of T cells derived from patients with pollinosis caused by tree pollens in springtime. In other words, the peptide of the present invention can induce proliferation of T cells or responses of T cells such as secretion of lymphokines, and/or can induce T-cell anergy (non-responsiveness). T-cell epitope sites on the allergen molecules can be identified using T-cell growth as an index in accordance with the method described in JP-A-Hei 8-47392. In particular, T-cell lines or T-cell clones, which are specifically reactive with Cha o 1 and Cha o 2, are established for every patient from peripheral lymphocytes of a patient with Japanese cypress pollinosis. The T-cell lines or T-cell clones are cultured in the presence of each peptide of the overlapping peptides. The epitope sites are identified by measuring the proliferation of T cells in the presence of the peptide (e.g., uptake of [$^3$H]thymidine into the cells) and calculating a stimulation index. The stimulation index (SI) used herein is obtained by dividing the radioactive level of [$^3$H]thymidine (cpm) taken up into the cells in the presence of the peptide by the level of [$^3$H]thymidine (cpm) taken up into the cells in the absence of the peptide (control). Based on the data obtained thus, a mean stimulation index for each peptide is calculated for each patient group. The peptides found to induce T-cell response and/or induce T-cell anergy are defined as having T-cell stimulating activity. The preferable T-cell epitope peptides of the present invention possess a T-cell stimulating activity and thus contain at least one T-cell epitope. Examples of the T-cell epitope peptide of Cha o 1 shown in FIG. 1 (specifically shown in FIG. 2, FIG. 3, and SEQ ID NO: 3 through SEQ ID NO: 37) include Peptide #1-2 (SEQ ID NO: 4), Peptide #1-4 (SEQ ID NO: 6), Peptide #1-5 (SEQ ID NO: 7), Peptide #1-6 (SEQ ID NO: 8), Peptide #1-7 (SEQ ID NO: 9), Peptide #1-8 (SEQ ID NO: 10), Peptide #1-10 (SEQ ID NO: 12), Peptide #1-11 (SEQ ID NO: 13), Peptide #1-12 (SEQ ID NO: 14), Peptide #1-14 (SEQ ID NO: 16), Peptide #1-15 (SEQ ID NO: 17), Peptide #1-16 (SEQ ID NO: 18), Peptide #1-19 (SEQ ID NO: 21), Peptide #1-20 (SEQ ID NO: 22), Peptide #1-21 (SEQ ID NO: 23), Peptide #1-22 (SEQ ID NO: 24), Peptide #1-23 (SEQ ID NO: 25), Peptide #1-24 (SEQ ID NO: 26), Peptide #1-25 (SEQ ID NO: 27), Peptide #1-26 (SEQ ID NO: 28), Peptide #1-27 (SEQ ID NO: 29), Peptide #1-30 (SEQ ID NO: 32), Peptide #1-31 (SEQ ID NO: 33), Peptide #1-32 (SEQ ID NO: 34), Peptide #1-33 (SEQ ID NO: 35), and Peptide #1-34 (SEQ ID NO: 36) (FIG. 4). Examples of the T-cell epitope peptide of Cha o 2 shown in FIG. 5 (specifically shown in FIG. 6, FIG. 7, and SEQ ID NO: 38 through SEQ ID NO: 88) include Peptide #2-5 (SEQ ID NO: 42), Peptide #2-7 (SEQ ID NO: 44), Peptide #2-8 (SEQ ID NO: 45), Peptide #2-9 (SEQ ID NO: 46), Peptide #2-10 (SEQ ID NO: 47), Peptide #2-11 (SEQ ID NO: 48), Peptide #2-12 (SEQ ID NO: 49), Peptide #2-13 (SEQ ID NO: 50), Peptide 2-14 (SEQ ID NO: 51), Peptide #2-15 (SEQ ID NO: 52), Peptide #2-16 (SEQ ID NO: 53), Peptide #2-17 (SEQ ID NO: 54), Peptide #2-18 (SEQ ID NO: 55), Peptide #2-19 (SEQ ID NO: 56), Peptide #2-20 (SEQ ID NO: 57), Peptide #2-21 (SEQ ID NO: 58), Peptide #2-22 (SEQ ID NO: 59), Peptide #2-23 (SEQ ID NO: 60), Peptide #2-24 (SEQ ID NO: 61), Peptide #2-25 (SEQ ID NO: 62), Peptide #2-26 (SEQ ID NO: 63), Peptide #2-27 (SEQ ID NO: 64), Peptide #2-30

(SEQ ID NO: 67), Peptide #2-31 (SEQ ID NO: 68), Peptide #2-32 (SEQ ID NO: 69), Peptide #2-33 (SEQ ID NO: 70), Peptide #2-34 (SEQ ID NO: 71), Peptide #2-35 (SEQ ID NO: 72), Peptide #2-36 (SEQ ID NO: 73), Peptide #2-37 (SEQ ID NO: 74), Peptide #2-38 (SEQ ID NO: 75), Peptide #2-40 (SEQ ID NO: 77), Peptide #2-41 (SEQ ID NO: 78), Peptide #2-42 (SEQ ID NO: 79), and Peptide #2-43 (SEQ ID NO: 80) (FIG. 8). More preferably, the T-cell epitope peptides have a mean stimulation index of 2.0 or more. Examples include Peptide #1-2 (SEQ ID NO: 4), Peptide #1-7 (SEQ ID NO: 9), Peptide #1-8 (SEQ ID NO: 10), Peptide #1-20 (SEQ ID NO: 22), Peptide #1-22 (SEQ ID NO: 24), Peptide #1-24 (SEQ ID NO: 26), Peptide #1-26 (SEQ ID NO: 28), Peptide #1-32 (SEQ ID NO: 34), Peptide #1-33 (SEQ ID NO: 35), and Peptide #1-34 (SEQ ID NO: 36), which are shown in FIG. 1, and Peptide #2-10 (SEQ ID NO: 47), Peptide #2-20 (SEQ ID NO: 57), Peptide #2-21 (SEQ ID NO: 58), Peptide #2-40 (SEQ ID NO: 77), Peptide #2-41 (SEQ ID NO: 78), Peptide #2-42 (SEQ ID NO: 79), and Peptide #2-43 (SEQ ID NO: 80), which are shown in FIG. 5. Most preferably, the T-cell epitope peptide has a minimum positively index of 100. Examples thereof include Peptide #1-7 (SEQ ID NO: 9), Peptide #1-22 (SEQ ID NO: 24), Peptide #1-32 (SEQ ID NO: 34), and Peptide #1-33 (SEQ ID NO: 35), which are shown in FIG. 1, and Peptide #2-10 (SEQ ID NO: 47), Peptide #2-20 (SEQ ID NO: 57), Peptide #2-40 (SEQ ID NO: 77), Peptide #2-41 (SEQ ID NO: 78), Peptide #2-42 (SEQ ID NO: 79), and Peptide #2-43 (SEQ ID NO: 80), which are shown in FIG. 5. The "positivity index" used herein is obtained by multiplying a mean stimulation index of a peptide by appearance frequency (%) of patients showing a T-cell response to the peptide.

To identify the epitope accurately, a peptide having the T-cell stimulating activity and thus containing at least one T-cell epitope may be modified by deleting any of the amino acid residues at the amino terminus or the carboxyl terminus of the peptide. The modified peptide may then be examined for any change in the T-cell stimulating activity. When two or more peptides that share the overlapping region exhibit the T-cell stimulating activity, a new T-cell epitope peptide containing all or part of the overlapping peptides is prepared, and its T-cell stimulating activity is measured in the same manner.

The T-cell epitope peptide of the present invention may possibly be immunologically associated with Cry j 1 or Cry j 2 in the T-cell cross-reactivity. Specifically, 1) the amino acid sequence of Cha o 1 has 80% homology to that of Cry j 1, and the amino acid sequence of Cha o 2 has 75% homology to that of Cry j 2; 2) the amino acid sequence of T-cell epitope peptide #1-2 of Cha o 1 (corresponding to amino acids 11-30, SEQ ID NO: 4, of mature type Cha o 1), which was identified in Example 5 of the present invention, is identical with the amino acid sequence of T-cell epitope peptide CJI-2 of Cry j 1 (corresponding to amino acids 11-30, of mature type Cry j 1; see FIG. 13 of JP-A-Hei 8-502163) except for two amino acid residues (Ala at position 12 of Cha o 1 corresponds to Ser of CJI-2, and Asp at position 15 of Cha o 1 corresponds to Ala of CJI-2); and 3) both cedar pollens and Japanese cypress pollens have a common antigenicity. For these reasons, the origin of the T-cell epitope of the present invention is not limited to Japanese cypress. The T-cell epitope peptide of the present invention is effective not only for Japanese cypress pollinosis but also for cedar pollinosis.

In the T-cell epitope peptide of the present invention, the amino acid residues that participate in recognizing the T-cell receptor can be determined by a known method (for example, measuring the change in the T-cell stimulating activity which might occur due to the substitution of amino acid residues). The amino acid residues found to be essential for an interaction with the T-cell receptor are substituted with other amino acid residues to antigen-specifically control the T-cell stimulating activity so that allergic inflammation can be suppressed (increase the reactivity of T cells, alter the lymphokine-producing pattern, anergy etc.). It has been reported that, when one amino acid residue at the T-cell recognition site of the T-cell epitope peptide of cedar pollen Cry j 1 was substituted with another amino acid residue (substituting Thr at position 399 with Val) in a human allergy model, the resulting analog peptide showed substantially the same T-cell growth and IL-4 production as those of a wild type peptide, but showed increased production of IFN-γ that suppressed the production of IgE antibodies (Ikagawa, S. et al., J. Aller. Clin. Immunol. 97, 54-64, 1996). It has further been revealed that a binding motif of HLA class II molecules consists of three to five amino acid residues arranged via one or two intermediary amino acid residues. When these residues consist of several kinds of specified amino acids, the peptide binds to the HLA class II molecules (Matsushita, S. et al., J. Exp. Med. 180: 877-883, 1994). Therefore, allergic inflammation can be prevented by determining the amino acid residues of the T-cell epitope peptide of the present invention, which are essential for the interaction with HLA class II molecules, by a known method, and substituting the relevant amino acid residues with other amino acid residues. Furthermore, the T-cell epitope peptide of the present invention can be modified so as to improve its solubility, thereby increasing its therapeutic or preventing effects or stability. Such modification includes substitution, deletion, and addition of the amino acid residues.

In the present invention, the T-cell epitope peptide preferably does not bind to IgE antibodies. Even if it binds to the IgE antibodies, the degree of binding is substantially lower than that of binding of the allergen of natural Japanese cypress pollens, from which the peptide is derived, to the antibodies.

The T-cell epitope peptide of the present invention preferably contains at least seven amino acid residues. These regions may be joined via a linker such as Arg-Arg or Lys-Lys that is sensitive to cleavage with an enzyme such as cathepsin or trypsin to enhance the sensitivity to processing by antigen-presenting cells. Thus, a peptide region can be produced to contain one or more T-cell epitopes. The T-cell epitope peptide of the present invention may be used in combination with other peptides such as a T-cell epitope peptide of Cry j 1 (JP-WA-Hei 8-502163) and/or a T-cell epitope peptide of Cry j 2 (JP-WA-Hei 8-47392).

When a peptide containing at least one T-cell epitope peptide of the present invention is administered to an individual sensitive to Japanese cypress pollens and/or an individual sensitive to both Japanese cypress and cedar pollens, the peptide can control the individual's allergic response to the allergen(s). Such a peptide is thus effective for peptide-based immunotherapy. In particular, the T-cell epitope peptide of the present invention in combination with the T-cell epitope peptide of cedar pollen is more effective for peptide-based immunotherapy for a patient with pollinosis caused by tree pollens in springtime, represented by cedar and Japanese cypress pollens.

The T-cell epitope peptide of the present invention may be used as a diagnostic tool for pollinosis caused by Japanese cypress pollen allergens or other tree pollens that are immunologically cross-reactive with Japanese cypress pollen allergens. In such an application, the T-cell epitope peptide of the present invention is added to peripheral lymphocytes collected from a patient in an amount of about 0.1 μg/ml to about 1 mg/ml, and preferably about 1 to about 300 μg/ml. After the mixture is incubated for a week, uptake of [³H]thymidine into the lymphocytes is assayed and assessed for diagnosis of pollinosis. The T-cell epitope peptide of the present invention may also be used to evaluate either the function of T cells or proliferation of T cells or both.

When the T-cell epitope peptide of the present invention is synthesized using recombinant DNA technology, host cells transformed with a nucleic acid containing a sequence coding for the peptide are cultured in a medium suitable for growing the host cells. The peptide can be harvested from the culture supernatant or from the host cells by a method known in the art. *E. coli*, yeasts, or mammal cells can be used as such host cells.

When the T-cell epitope peptide of the present invention is used in peptide-based immunotherapy for patients with pollinosis, the peptide may be administered together with pharmaceutically acceptable diluents or carriers. The "patient with pollinosis" as used herein includes patients with cedar pollinosis who show immunological cross-reactivity with the allergen of Japanese cypress pollen. The T-cell epitope peptide of the present invention can be administered in a simple manner, for example, by injection (subcutaneous or intravenous), instillation, rhinenchysis, oral administration, inhalation, or percutaneous administration. In the case of injection, a single dose of the peptide ranges preferably from about 1 µg to about 30 mg, and more preferably from about 20 µg to about 10 mg.

BRIEF DESCRIPTION OF THE DRAWINGS

FIG. 2 shows overlapping peptides (#1-1 (SEQ ID NO:3) to #1-28 (SEQ ID NO:30)) of Cha o 1.

FIG. 3 shows overlapping peptides (#1-29 (SEQ ID NO:31) to #1-35 (SEQ ID NO:37)) of Cha o 1.

FIG. 4 shows peptides containing T-cell epitopes of Cha o 1.

FIG. 6 shows overlapping peptides (#2-1 (SEQ ID NO:38) to #2-27 (SEQ ID NO:64)) of Cha o 2.

FIG. 7 shows overlapping peptides (#2-28 (SEQ ID NO:65) to #2-51 (SEQ ID NO:88)) of Cha o 2.

FIG. 8 shows peptides containing T-cell epitopes of Cha o 2.

BEST MODE FOR IMPLEMENTING THE INVENTION

Examples of the present invention will be described below, but are not to be construed to limit the scope of the present invention.

EXAMPLE 1

Synthesis of Overlapping Peptides

Figure 5:
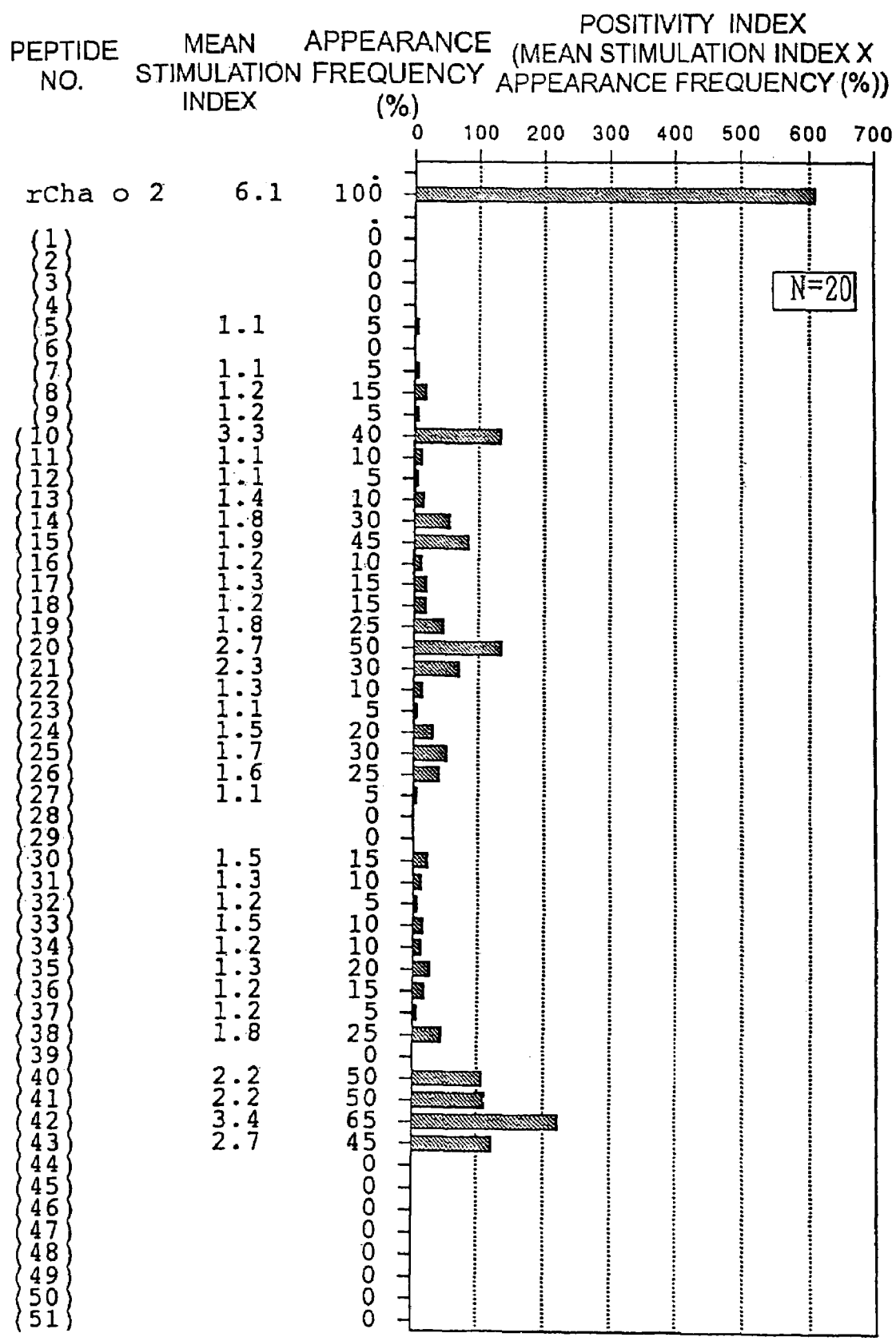
FIG. 5 shows T-cell epitope peptides of Japanese cypress pollen allergen, Cha o 2, and a positivity index of each peptide.

Based on the amino acid sequences of Japanese cypress pollen allergens Cha o 1 (SEQ ID NO: 1) and Cha o 2 (SEQ ID NO: 2), overlapping peptides consisting of 20 amino acid residues (14 residues in Peptide #1-35 (SEQ ID NO: 37) and Peptide #2-51 (SEQ ID NO: 88), each containing 10 overlapping residues) were synthesized by the Fmoc method using a peptide synthesizer (PSSM-8, Shimadzu Seisakusho Ltd.). Thirty-five overlapping peptides were prepared for Cha o 1 (FIG. 1, SEQ ID NO: 3 through SEQ ID NO: 37), and 51 kinds, for Cha o 2 (FIG. 5, SEQ ID NO: 38 through SEQ ID NO: 88). The synthesized peptides were all purified by high-performance liquid chromatography (HPLC) using an ODS column. The purity was 90% or higher in all of the peptides. The molecular weights of the purified peptides were identified by using a LASERMAT 2000 (Finnigan MAT Ltd.).

EXAMPLE 2

Expression of the Recombinant Proteins in *E. coli*

Using a PCR technique, cDNA was amplified from plasmid DNA, in which Cha o 1 cDNA or Cha o 2 cDNA encoding a Japanese cypress pollen antigen had been cloned (Japanese Patent Application No. Hei 6-335089). A restriction enzyme recognition site was attached to the terminus of each cDNA. This DNA fragment was inserted into a histidine-tagged protein expression vector, pQE9, and the resulting vector was used to transform *E. coli* M15 (pREP4). Expression of the transforming gene was confirmed for ampicillin-resistant clones by SDS-polyacrylamide gel electrophoresis. The protein expressed was purified using a Ni-NTA agarose affinity column.

EXAMPLE 3

Establishment of T-cell Line

A T-cell line on Cha o 1 was established as follows. Peripheral lymphocytes collected from 19 patients found positive to Japanese cypress pollinosis using Ala STAT (Nippon DPC Corporation) or CAP-RAST (Pharmacia) were separated by specific gravity centrifugation using Ficoll-Paque. The lymphocytes ($2\times10^6$ cells) were suspended in RPMI 1640 medium (GIBCO, Inca) supplemented with 2 ml of plasma from the same patient (10%) or human AB type serum (20%, Banpoh Tsusho Co., Ltd.). The suspension was incubated in a 24-well plate for 3 to 10 days (37° C., $CO_2$ incubator, TABAI, Inc.), together with 10 to 30 µg/ml of the recombinant Cha o 1 obtained in Example 2 or with a mixture of the overlapping peptides (0.01 to 1 µM) obtained in Example 1. When T cells activated by Cha o 1 stimulation were verified microscopically, 5 U/ml of IL-2 (Boehringer Mannheim) was added to the system, followed by incubation overnight. On the next day, the medium was replaced with fresh RPMI 1640 medium supplemented with 20 U/ml of IL-2, 10% or 20% human AB type serum. Incubation was continued for about 10 days with the medium being replaced every day in the same manner. The resulting T-cell line was examined for its specificity, and a sample of the T-cell line was frozen and stored. A T-cell line stimulated by Cha o 2 was also established from 20 patients with Japanese cypress pollinosis in the same way.

EXAMPLE 4

Establishment of Antigen-presenting Cells

A lymphoblastoid cell line (B cell line) transformed by infecting EB virus B lymphocytes with EB virus (Epstein-Barr virus, EBV) was established to serve as antigen-presenting cells. First, EBV-producing B-95-8 cells (marmoset, ATCC CRL 1612) were cultured in RPMI 1640 medium supplemented with 20% inactivated fetal calf serum (FCS, GIBCO Inc.). The culture supernatant was filtered through a 0.22 µm sterile filter. The filtrate was frozen and stored at −80° C. Next, 1 ml of EBV solution was added to lymphocytes (2×10⁶ cells) of a patient with Japanese cypress pollinosis, and the mixture was maintained at 37° C. for 30 minutes for infection. The EBV-infected cells were washed twice and then incubated for about 20 days in 20% FCS-RPMI 1640 medium supplemented with a final concentration of 200 ng/ml of Cyclosporin (Sandoz Pharmaceutical Co., Ltd.). After the cell mass was observable by the naked eye, incubation was continued in 20% FCS-RPMI 1640 medium for another 20 days. The resulting cells were frozen and stored until they were used.

EXAMPLE 5

Identification of T-cell Epitope Peptide

The cultured B cell line established in Example 4 was treated with 50 μg/ml of mitomycin C (Sandoz Pharmaceutical Co., Ltd.) for 30 minutes or exposed to an X ray (50 g ray), followed by washing four times with RPMI 1640 medium. After the B cells were inoculated on a 96-well plate (10,000 cells/well), the recombinant Cha o 1 or Cha o 2 was added thereto in a final concentration of 10 g/ml. To the control group was added a hemolytic *streptococcus* cell wall antigen (SCW) in a final concentration of 10 μg/ml, *Candida albicans* antigen (CA) in a final concentration of 10 μg/ml, and a Tuberculin antigen (PPD) in a final concentration of 1 μg/ml). Subsequently, the T-cell line (20,000 cells/well) from the same patient, whose B cell line had been established, was inoculated into each well. After a 48-hour incubation, 0.5 μCi [3H]thymidine was added to each well, and incubation was continued for a further 16 hours. After the cells were collected on a glass filter using a cell harvester (Berthold) uptake of [3H]thymidine into the cells was measured with a liquid scintillation counter to confirm the cell growth response.

Figure 1:
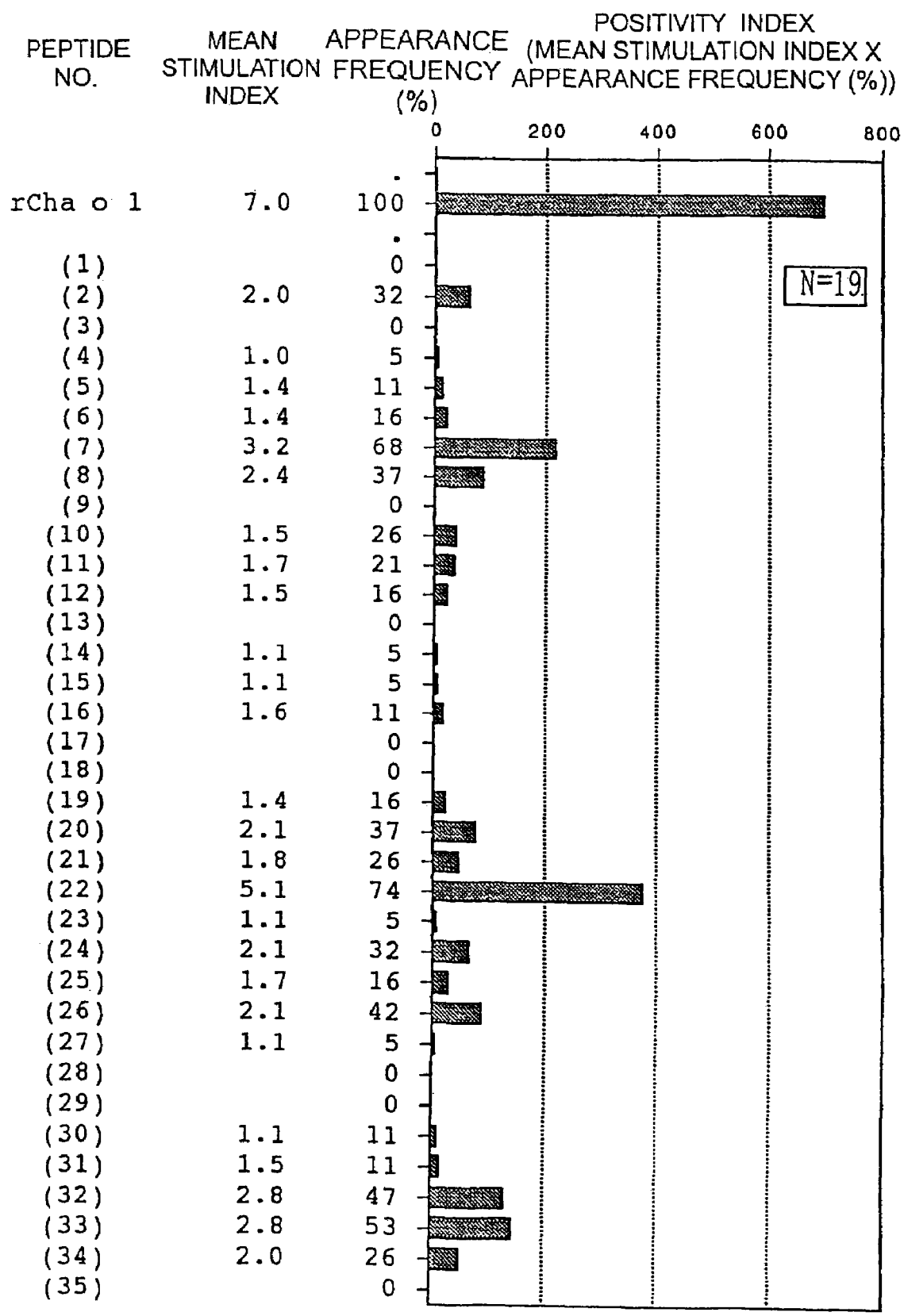
FIG. 1 shows T-cell epitope peptides of the Japanese cypress pollen allergen, Cha o 1, and a positivity index of each peptide.

After the T-cell line was confirmed to have proliferated specifically in response to Cha o 1 or Cha o 2, the growth response of the T-cell line to each of the overlapping peptides (final concentration of 1 μM) was examined in the same manner as above using the T-cell line established in Example 3. A mean stimulation index of the T-cell line in growth response to the overlapping peptides, an appearance frequency, and a positivity index calculated therefrom are shown in FIGS. 1 and 5.

In addition, growth response of the T-cell line (N=17) to modified sequences (SEQ ID NO: 89 and NO: 90) that corresponded to the amino acid sequences #2-11 and #2-12 in which one amino acid residue had been substituted, was examined. These two modified sequences exhibited T-cell stimulating activity of 1.6 and 1.2 in terms of the stimulation index, 16% and 11% in terms of the appearance frequency, and 25.6 and 13.2 in terms of the positivity index. As demonstrated above, the T-cell epitope peptide of the present invention retained its T-cell stimulating activity even when one or more amino acid residues were mutated, and the activity was enhanced in some cases.

INDUSTRIAL APPLICABILITY

The present invention provides peptides containing at least one T-cell epitope of Cha o 1 or Cha o 2, which are major allergens of Japanese cypress pollens. The present invention further includes a peptide fragment of other tree pollens showing immunological T-cell cross-reactivity with the peptides. These peptides are effective for peptide-based immunotherapy of pollinosis caused by tree pollens in springtime as represented by cedar and Japanese cypress pollens.

The invention claimed is:

1. A method for treating pollinosis caused by tree pollen in springtime, the method comprising administering a peptide to a patient that has pollinosis in the pollen-scattering season, wherein the peptide is derived from Japanese cypress pollen allergen Cha o 2 and consists of:
   (i) (a) an amino acid sequence selected from the group consisting of SEQ ID NO:42, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ IL) NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ TD NO:63, SEQ ID NO:64, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:77, SEQ ID NO:78, SEQ ID NO:79, and SEQ ID NO:80, said amino acid sequence having T-cell stimulating activity; or (i) (b) a fragment of the amino acid sequence of (i)(a), the fragment being selected from fragments of the amino acid sequences listed in (i)(a), wherein each of the fragments has T-cell stimulating activity equivalent to that of the corresponding amino acid sequence of (i)(a); or
   (ii) a combination of sequences, the sequences being selected from the amino acid sequences listed in (i)(a) and the amino acid sequence fragments recited in (i)(b).

2. A method for treating pollinosis caused by tree pollen in springtime, the method comprising administering a peptide to a patient that has pollinosis in the pollen-scattering season, wherein the peptide is derived from Japanese cypress pollen allergen Cha o 2 and consists of a combination of two or more amino acid sequences and a linker sensitive to enzyme cleavage between each amino acid sequence, wherein said two or more amino acid sequences of the combination are:
   sequences selected from the group consisting of SEQ ID NO:42, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID No:57, SEQ ID No:58, SEQ ID NO:59, SEQ ID NO:60, SEQ ID NO:61, SEQ ID NO:62, SEQ ID NO:63, SEQ ID NO:64, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:77, SEQ ID NO:78, SEQ ID NO:79, and SEQ ID NO:80, the sequences having T-cell stimulating activity; or
   fragments of sequences selected from the set consisting of SEQ ID NO:42, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:77, SEQ ID NO:78, SEQ ID NO:79, and SEQ ID NO:80, each fragment having T-cell stimulating activity equivalent to that of the corresponding sequence.

3. The method of claim 2, wherein said linker is Arg-Arg or Lys-Lys.

4. The method of claim 1, wherein the peptide consists of:
   (A) an amino acid sequence selected from sequences of the group consisting of: SEQ ID NO: 42, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 77, SEQ ID NO: 78, SEQ ID NO: 79, and SEQ ID NO: 80; or
   (B) a combination of amino acid sequences selected from the sequences listed in (A).

5. The method of claim 1, wherein the peptide consists of:
   (x) an amino acid sequence selected from sequences of the group consisting of SEQ ID NO: 47, SEQ ID NO: 57, SEQ ID NO: 58, SEQ ID NO: 77, SEQ ID NO: 78, SEQ ID NO: 79, and SEQ ID NO: 80; or
   (y) a combination of amino acid sequences selected from the sequences listed in (x).

6. The method of claim 1, wherein the peptide consists of:
   (X) an amino acid sequence selected from sequences of the group consisting of SEQ ID NO: 47, SEQ ID NO: 57, SEQ ID NO: 77, SEQ ID NO: 78, SEQ ID NO: 79, and SEQ ID NO: 80; or
   (Y) a combination of amino acid sequences selected from the sequences listed in (X).

* * * * *

UNITED STATES PATENT AND TRADEMARK OFFICE
CERTIFICATE OF CORRECTION

PATENT NO. : 7,547,440 B2  Page 1 of 1
APPLICATION NO. : 12/163896
DATED : June 16, 2009
INVENTOR(S) : Kohsuke Kino It is certified that error appears in the above-identified patent and that said Letters Patent is hereby corrected as shown below:

In Col. 5, line 44: before "be", delete "possibly"

In Col. 8, line 3: before "for", delete "kinds"

In Col. 8, line 61: after "infecting", delete "EB virus"

In Col. 55, line 21: in Claim 1, delete "IL)" and insert -- ID --, therefor

In Col. 55, line 25: in Claim 1, delete "TD" and insert -- ID --, therefor

In Col. 55, line 55: in Claim 2, before ":57" delete "No" and insert -- NO --, therefor In Col. 55, line 55: in Claim 2, before ":58" delete "No" and insert -- NO --, therefor Signed and Sealed this Tenth Day of November, 2009

David J. Kappos
*Director of the United States Patent and Trademark Office*